(12) United States Patent
Mitsunami

(10) Patent No.: US 11,318,263 B2
(45) Date of Patent: May 3, 2022

(54) MESH NEBULIZER AND MEDICINAL LIQUID PACK

(71) Applicant: OMRON HEALTHCARE CO., LTD., Muko (JP)

(72) Inventor: Yukiko Mitsunami, Kyoto (JP)

(73) Assignee: OMRON HEALTHCARE CO., LTD., Kyoto (JP)

(*) Notice: Subject to any disclaimer, the term of this patent is extended or adjusted under 35 U.S.C. 154(b) by 729 days.

(21) Appl. No.: 16/280,080

(22) Filed: Feb. 20, 2019

(65) Prior Publication Data

US 2019/0175845 A1    Jun. 13, 2019

Related U.S. Application Data

(63) Continuation of application No. PCT/JP2017/028910, filed on Aug. 9, 2017.

(30) Foreign Application Priority Data

Sep. 20, 2016 (JP) .............................. JP2016-183462

(51) Int. Cl.
*A61M 11/00* (2006.01)
*A61M 15/00* (2006.01)
*B05B 17/06* (2006.01)

(52) U.S. Cl.
CPC ...... *A61M 11/005* (2013.01); *A61M 15/0023* (2014.02); *A61M 15/0028* (2013.01);
(Continued)

(58) Field of Classification Search
CPC .. A61M 11/005; A61M 11/00; A61M 11/001; A61M 11/002; A61M 11/003;
(Continued)

(56) References Cited

U.S. PATENT DOCUMENTS

| 8,353,287 B1 | 1/2013 | Hollen et al. |
| 2003/0062038 A1* | 4/2003 | Tanaka ................. A61M 15/00 128/200.14 |

(Continued)

FOREIGN PATENT DOCUMENTS

| JP | 2010-119845 A | 6/2010 |
| JP | 2013-252261 A | 12/2013 |

(Continued)

OTHER PUBLICATIONS

Official Communication issued in International Patent Application No. PCT/JP2017/028910, dated Oct. 31, 2017.

*Primary Examiner* — Joseph D. Boecker
*Assistant Examiner* — Brian T Khong
(74) *Attorney, Agent, or Firm* — Keating and Bennett, LLP

(57) ABSTRACT

A mesh nebulizer that nebulizes and ejects a medicinal liquid through a mesh portion, includes a main body including a vibration portion including a vibration surface, and a medicinal liquid pack to be detachably mounted on the main body. The medicinal liquid pack includes a lid in which the mesh portion is provided, and a medicinal liquid container that includes a recessed portion that is open toward the mesh portion and is covered by the lid, the medicinal liquid being contained in the recessed portion. At least a portion of a bottom surface of the recessed portion of the medicinal liquid container that is to oppose the vibration surface is made of a stretchable material. When the medicinal liquid pack is mounted on the main body, the stretchable material of the bottom surface stretches, allowing the vibration surface to approach the mesh portion of the lid.

6 Claims, 7 Drawing Sheets

(52) U.S. Cl.
CPC ......... *A61M 15/0085* (2013.01); *B05B 17/06* (2013.01); *A61M 2202/0468* (2013.01); *A61M 2205/0216* (2013.01); *A61M 2205/123* (2013.01); *A61M 2205/8206* (2013.01); *A61M 2210/0625* (2013.01)

(58) Field of Classification Search
CPC .. A61M 11/006; A61M 11/007; A61M 11/04; A61M 11/041; A61M 11/042; A61M 11/08; A61M 15/0001; A61M 15/001; A61M 15/0023; A61M 15/0025; A61M 15/0026; A61M 15/0028; A61M 15/0085; B05B 17/06; B05B 17/0607; B05B 17/0615; B05B 17/0623; B05B 17/063; B05B 17/0638; B05B 17/0646
See application file for complete search history.

(56) References Cited

U.S. PATENT DOCUMENTS

2012/0259277 A1    10/2012  Shay et al.
2016/0213866 A1*   7/2016   Tan ................... A61M 15/0085

FOREIGN PATENT DOCUMENTS

| JP | 2014-4208 A | 1/2014 |
| JP | 2014-4211 A | 1/2014 |

\* cited by examiner

MESH NEBULIZER AND MEDICINAL LIQUID PACK

CROSS REFERENCE TO RELATED APPLICATIONS

This application claims the benefit of priority to Japanese Patent Application No. 2016-183462 filed on Sep. 20, 2016 and is a Continuation Application of PCT Application No. PCT/JP2017/028910 filed on Aug. 9, 2017. The entire contents of each application are hereby incorporated herein by reference.

BACKGROUND OF THE INVENTION

1. Field of the Invention

The present invention relates to a mesh nebulizer, and more specifically relates to a mesh nebulizer that nebulizes and ejects a liquid supplied between a vibration surface and a mesh portion, through the mesh portion.

Also, the present invention relates to a medicinal liquid pack that is suitable for forming such a mesh nebulizer.

2. Description of the Related Art

Conventionally, as this kind of mesh nebulizer, as disclosed in JP 2014-4208A, a mesh nebulizer has been known which includes a horn vibrator in a main body and a mesh cap that is attached to the main body so as to be detachable and so as to be able to open and close (rotate). In the state in which the mesh cap is attached to the main body and is closed, the vibration surface of the horn vibrator and the mesh portion of the mesh cap oppose each other. In this state, medicinal liquid is supplied between the vibration surface and the mesh portion, and a driving voltage is applied to the horn vibrator, whereby the vibration surface is vibrated. Accordingly, the medicinal liquid is nebulized and ejected through the mesh portion.

However, with the above-described mesh nebulizer, each time after use, the mesh cap needs to be removed from the main body and the mesh cap including the mesh portion needs to be washed, disinfected, and dried. For this reason, there is a problem in that maintenance is troublesome for a user. Furthermore, since the mesh cap is a precision component, there are problems in that the mesh cap is easily broken through washing and in that the mesh cap is difficult to wash. Also, there is a problem in that the mesh portion will be unhygienic and its nebulization efficiency will decrease if not washed correctly.

SUMMARY OF THE INVENTION

Preferred embodiments of the present invention provide hygienic mesh nebulizers each structured to make cleaning the power source easier for a user without reducing nebulization efficiency.

Also, other preferred embodiments of the present invention provide medicinal liquid packs suitable for forming such mesh nebulizers.

A mesh nebulizer according to a preferred embodiment of the present invention that nebulizes and ejects a medicinal liquid through a mesh portion includes a main body including a vibration portion including a vibration surface, and a medicinal liquid pack to be detachably mounted on the main body, wherein the medicinal liquid pack includes a lid in which the mesh portion is located, a medicinal liquid container including a recessed portion that is open toward the mesh portion and is covered by the lid, the medicinal liquid that is to be supplied onto the vibration surface being contained in the recessed portion, at least a portion of a bottom surface of the recessed portion of the medicinal liquid container that is to oppose the vibration surface is made of a stretchable material, and when the medicinal liquid pack is mounted on the main body, the stretchable material of the bottom surface stretches, allowing the vibration surface to approach the mesh portion of the lid.

A planar shape of the recessed portion widely encompasses a ring shape, such as a circle or a rounded-corner rectangle (a rectangle with rounded corners).

With a mesh nebulizer according to a preferred embodiment of the present invention, at the time of use, the medicinal liquid pack is detachably mounted on the main body in advance. The medicinal liquid pack preferably includes a lid in which the mesh portion is located, and a medicinal liquid container that includes a recessed portion that opens toward the mesh portion and is covered by the lid, the medicinal liquid being contained in the recessed portion. Here, at least the portion of the bottom surface of the recessed portion of the medicinal liquid container that is to oppose the vibration surface is made of a stretchable material. With this configuration, when the medicinal liquid pack is mounted on the main body, the stretchable material of the bottom surface stretches, and thus the vibration surface is able to approach the mesh portion of the lid.

During use, the medicinal liquid is supplied onto the vibration surface of the vibration portion. Accordingly, the medicinal liquid is supplied between the vibration surface and the mesh portion. Then, the vibration surface is vibrated due to a drive voltage being applied to the vibration portion. Accordingly, the medicinal liquid is nebulized and ejected through the mesh portion.

After use, the medicinal liquid pack is removed from the main body and thrown away.

Thus, since a new medicinal liquid pack is mounted in a mesh nebulizer of a preferred embodiment of the present invention each time it is used, there is no need to wash the mesh portion. Accordingly, it is hygienic and maintenance is made easier for the user without reducing the nebulization efficiency. Furthermore, since a new mesh portion is used each time, it is hygienic and the nebulization efficiency does not decrease.

With a mesh nebulizer of a preferred embodiment of the present invention, the main body further includes an inner circumferential wall surrounding the vibration surface, an outer circumferential wall rotatable about the inner circumferential wall concentrically with the inner circumferential wall, and a holder that includes a cylindrical circumferential wall that is to be inserted between the inner circumferential wall and the outer circumferential wall and is to receive and hold the medicinal liquid pack through an opening in the circumferential wall, the mesh nebulizer including an elevator to raise or lower the holder with respect to the inner circumferential wall accompanying rotation of the outer circumferential wall of the main body about the inner circumferential wall.

With the mesh nebulizer of this preferred embodiment, a cylindrical holder in which the medicinal liquid pack is to be held is included in the main body. In the holder, an opening through which the medicinal liquid pack is to be taken out and inserted is provided in a portion of the circumferential wall, and the circumferential wall is located inside of the outer circumferential wall. Furthermore, an elevator that raises or lowers the holder with respect to the inner circumferential wall accompanying rotation of the outer circumferential wall about the inner circumferential wall is included.

Accordingly, when the outer circumferential wall is rotated about the inner circumferential wall by the user, the holder is raised and the opening of the circumferential wall located on the inside of the outer circumferential wall is exposed. Next, after mounting the medicinal liquid pack via the opening, the user rotates the outer circumferential wall about the inner circumferential wall in the direction opposite to the direction used when the holder is raised. Upon doing so, the elevator is able to lower the holder, and the opening of the circumferential wall is able to be located inside of the outer circumferential wall.

Here, when the medicinal liquid pack is mounted on the main body, the outer circumferential wall is rotated about the inner circumferential wall, and if the holder is lowered with respect to the inner circumferential wall by the elevator, the bottom wall of the medicinal liquid pack approaches and comes into contact with the vibration surface. Then, the stretchable material of the bottom surface of the medicinal liquid pack stretches and the vibration surface approaches the mesh portion of the lid. Also, when the medicinal liquid pack is removed from the main body, the outer circumferential wall is rotated about the inner circumferential wall, and if the holder is raised with respect to the inner circumferential wall by the elevator, the medicinal liquid pack separates from the vibration surface. In this way, the user can detach and attach the medicinal liquid pack from and to the main body.

With a mesh nebulizer of a preferred embodiment of the present invention, the elevator includes a first screw provided on an outer circumferential surface of the holder, and a second screw provided on an inner surface of the outer circumferential wall of the main body so as to be able to engage with the first screw.

With the mesh nebulizer of this preferred embodiment, the first screw is provided on the outer circumferential surface of the holder, and the second screw that engages with the first screw is provided on the inner surface of the outer circumferential wall. For this reason, the holder is able to be raised and lowered by rotating the outer circumferential wall. Furthermore, since the screws are defined by grooves in surfaces, the holder is able to be formed easily and is not likely to break.

In another preferred embodiment of the present invention, a medicinal liquid pack to be mounted in the above-described mesh nebulizer, includes a lid in which the mesh portion is provided, and a medicinal liquid container that includes a recessed portion that is open toward the mesh portion and is covered by the lid, the medicinal liquid that is to be supplied onto the vibration surface being contained in the recessed portion, wherein at least a portion of a bottom surface of the recessed portion of the medicinal liquid container that is to oppose the vibration surface is made of a stretchable material.

A medicinal liquid pack according to a preferred embodiment of the present invention is suitable for the mesh nebulizer.

With a medicinal liquid pack according to a preferred embodiment of the present invention, the lid includes a flange portion extending to the outside from an upper edge of the medicinal liquid container, and when the medicinal liquid pack is mounted on the main body, the flange portion of the lid is supported by an upper edge of an inner circumferential wall surrounding the vibration surface of the main body.

With the medicinal liquid pack of this preferred embodiment, the lid includes a flange portion extending to the outside from the upper edge of the medicinal liquid container. For this reason, when the medicinal liquid pack is mounted on the main body, the flange portion of the lid is able to be supported by the upper edge of the inner circumferential wall of the main body.

With a medicinal liquid pack of a preferred embodiment of the present invention, the lid has a flat shape, the recessed portion includes a deep first region in which the medicinal liquid is stored, and a second region that is shallower than the first region, and the bottom surface of the recessed portion of the medicinal liquid container that is to oppose the vibration surface is located in the second region.

With the medicinal liquid pack of this preferred embodiment, the recessed portion includes a shallow region and a deep region, and the bottom surface of the recessed portion of the medicinal liquid container that is to oppose the vibration surface is located in the shallow region. With this configuration, the vibration surface more easily approaches the mesh portion of the lid.

As is evident from the description above, the mesh nebulizers according to preferred embodiments of the present invention are easier for the user to maintain. Furthermore, since a new mesh portion is used each time, it is hygienic and the nebulization efficiency does not decrease. The medicinal liquid packs according to preferred embodiments of the present invention are suitable for such inventive mesh nebulizers.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described in detail with reference to the drawings.

Figure 1:
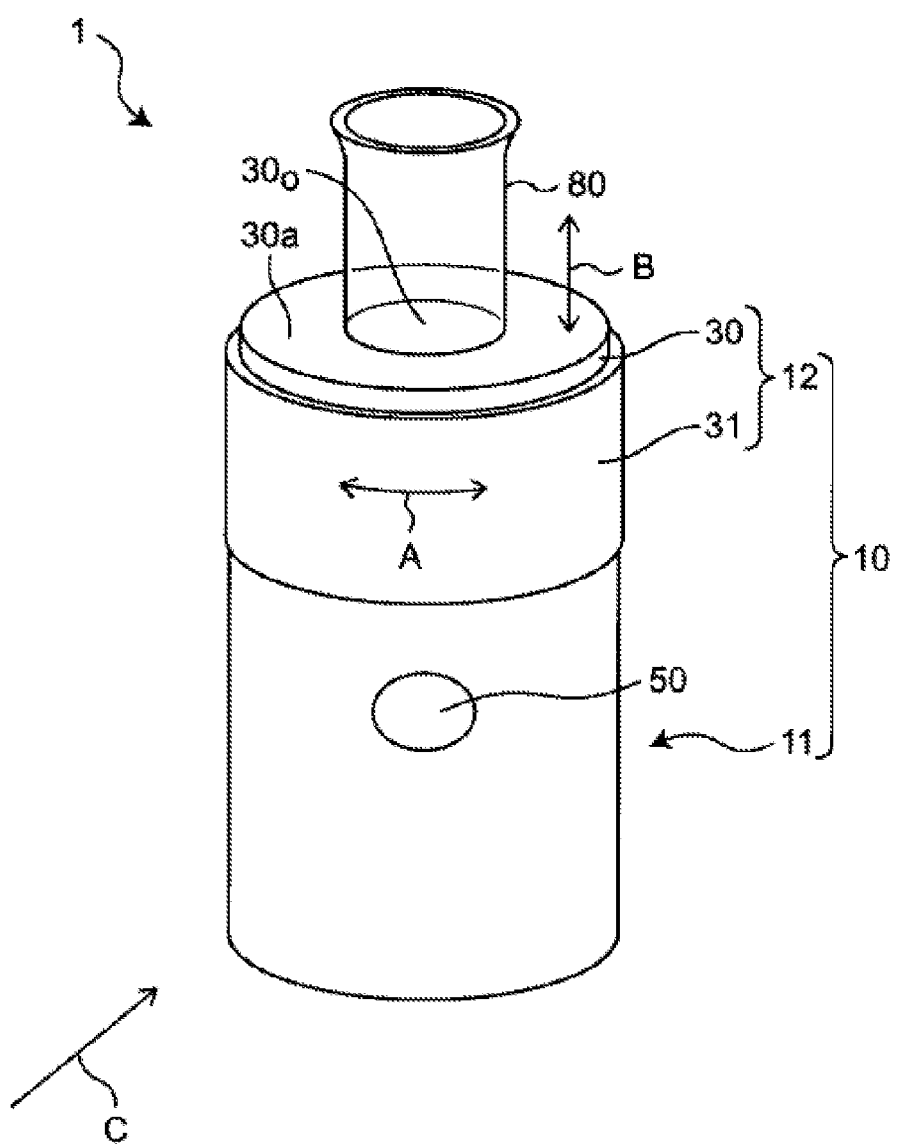
FIG. 1 shows an oblique view of a mesh nebulizer of a preferred embodiment of the present invention.

FIG. 1 shows an oblique view of a mesh nebulizer (indicated overall by the reference numeral 1) of a preferred embodiment of the present invention.

As shown in FIG. 1, the mesh nebulizer 1 includes a main body lower portion 11 having an approximately circular column-shaped outer shape and a main body upper portion 12 that is to be fit into the main body lower portion 11 and has an approximately circular column-shaped outer shape. Here, the main body upper portion 12 includes an outer circumferential wall 31 that can fit into the main body lower portion 11 and can rotate in a circumferential direction (arrow A) and a cylindrical holder 30 that rises and lowers in the up-down direction (arrow B) according to the rotation of the outer circumferential wall 31. A later-described medicinal liquid pack 20 is held in this holder 30. Note that the main body lower portion 11 and the main body upper portion 12 define a main body 10.

As shown in FIG. 1, the front surface of the main body lower portion 11 is provided with a power switch 50 to switch on and off the power of the power source 1. Also, a later-described control system is mainly mounted inside of the main body lower portion 11. Furthermore, an opening 30o is provided on an upper surface 30a of the holder 30, and, for example, a mouthpiece 80 is detachably mounted in the opening 30o.

Figure 2A:
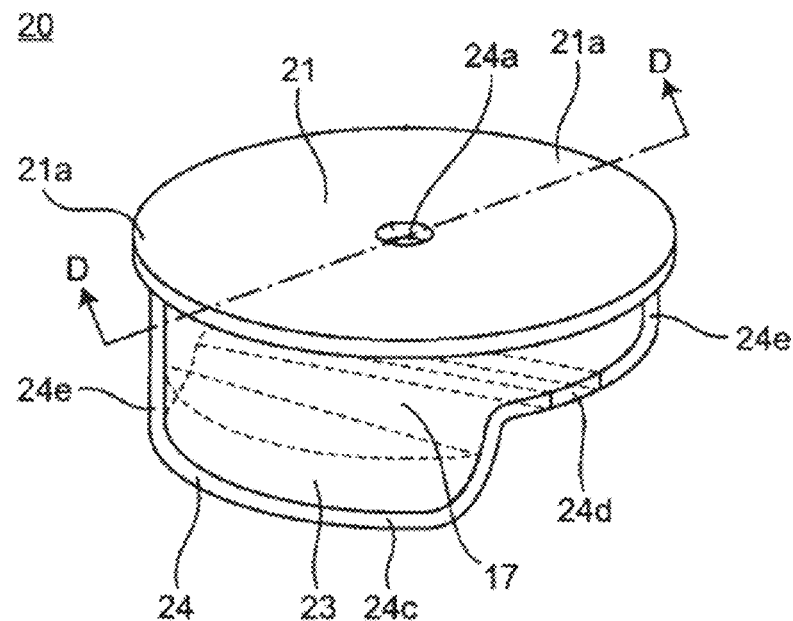
FIG. 2A is a schematic view of a medicinal liquid pack to be mounted on the mesh nebulizer shown in FIG. 1.
Figure 2B:
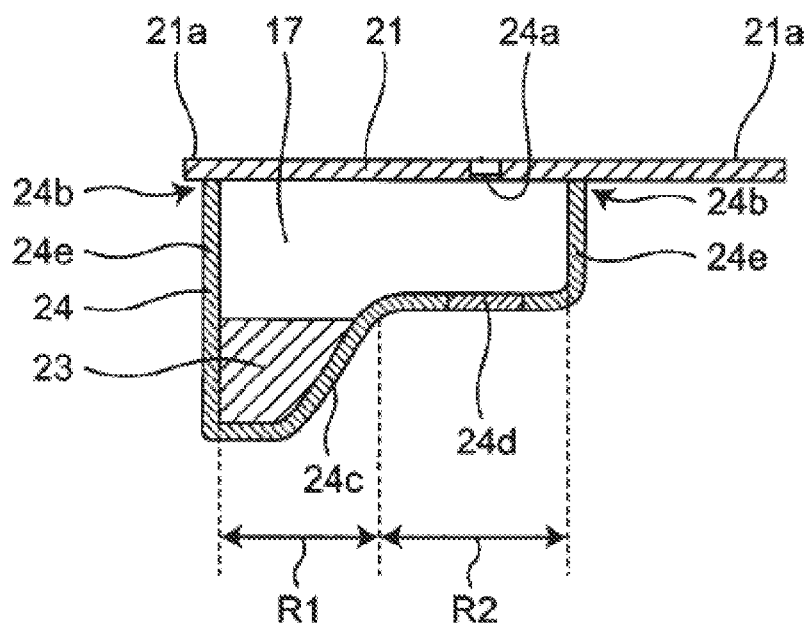
FIG. 2B is a vertical cross-sectional diagram obtained by cutting along line D-D in FIG. 2A.

FIG. 2A is a perspective view of the medicinal liquid pack 20 to be mounted in the mesh nebulizer 1 shown in FIG. 1, and FIG. 2B is a vertical cross-sectional diagram obtained by cutting along line D-D in FIG. 2A. As shown in FIGS. 2A and 2B, the medicinal liquid pack 20 preferably includes a medicinal liquid container 24 including a recessed portion 17, and a lid 21 that covers the medicinal liquid container 24 and has an approximately flat shape.

As shown in FIGS. 2A and 2B, the medicinal liquid container 24 of the medicinal liquid pack 20 includes a deep first region R1 in which a medicinal liquid 23 is stored, and a second region R2 that is shallower than the first region R1. Here, a bottom surface 24c of the recessed portion 17 of the medicinal liquid container 24 that is to oppose a later-described vibration surface 43 is provided in the second region. Also, a portion 24d of the bottom surface 24c of the recessed portion 17 of the medicinal liquid container 24 that is to oppose the later-described vibration surface 43 is made of a stretchable material. With this configuration, when the medicinal liquid pack 20 is mounted in the main body 10, the stretchable material of the bottom surface 24c stretches, and the vibration surface 43 is thus allowed to approach a mesh portion 24a of the lid 21.

The mesh portion 24a is preferably located in the approximate center of the lid 21 of the medicinal liquid pack 20. The lid 21 includes a flange portion 21a extending to the outside from an upper edge 24b of a side wall 24e of the medicinal liquid container 24.

Figure 3:
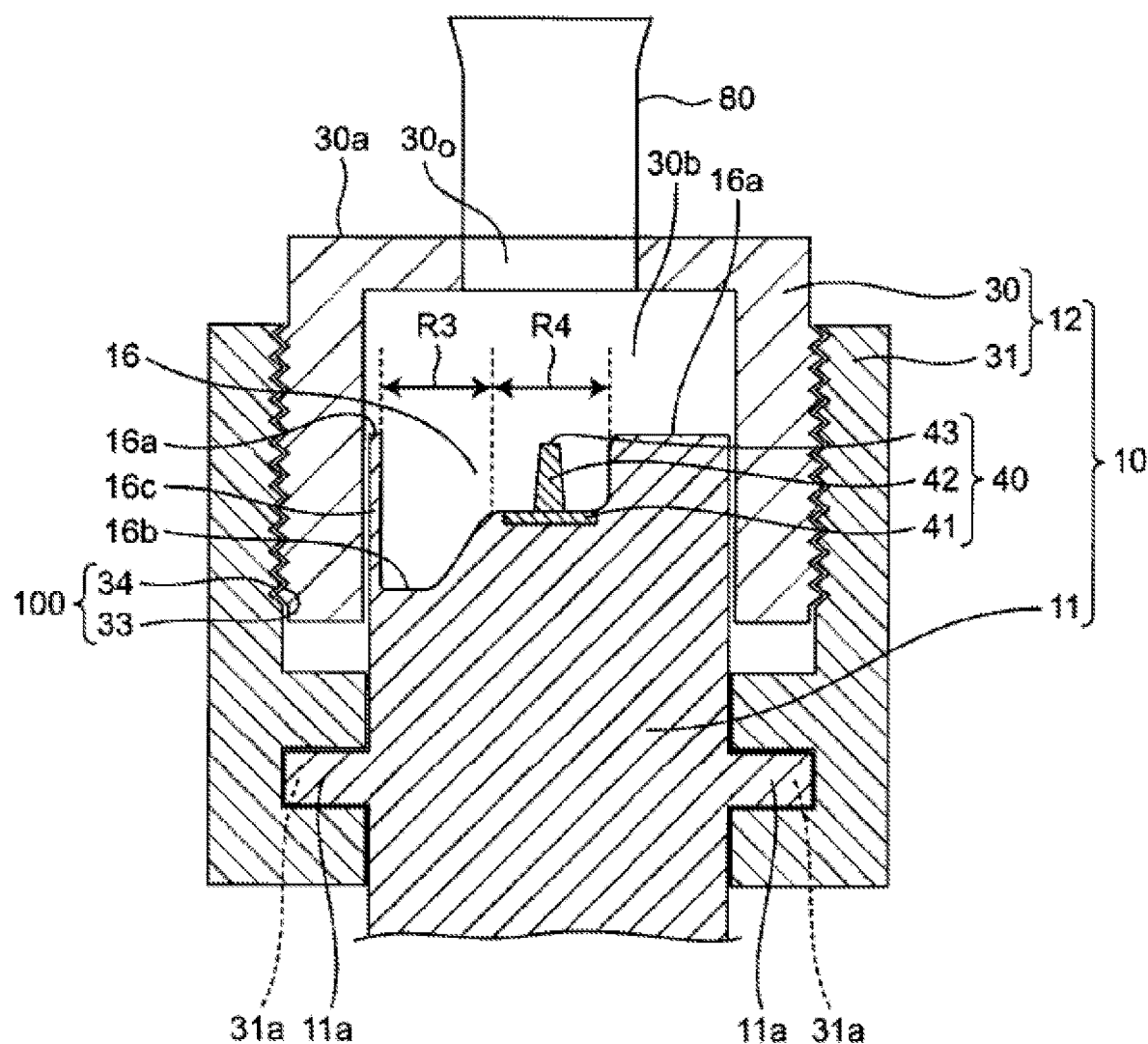
FIG. 3 is a diagram showing a portion of a vertical cross-section of the mesh nebulizer shown in FIG. 1, viewed from the right side.

FIG. 3 is a diagram showing a portion of a vertical cross-section of the mesh nebulizer 1 shown in FIG. 1, viewed from the right side (the direction indicated by the arrow C in FIG. 1). FIG. 3 shows the mesh nebulizer 1 in a state in which the medicinal liquid pack 20 is not mounted in the main body 10 of the mesh nebulizer 1.

As shown in FIG. 3, an inner circumferential wall 16c that surrounds the vibration surface 43 is included in the main body lower portion 11. Here, the vibration surface 43 and the inner circumferential wall 16c preferably are integrally formed. The main body upper portion 12 includes an outer circumferential wall 31 that is able to rotate about the inner circumferential wall 16c concentrically with the inner circumferential wall 16c of the main body lower portion 11.

Also, a protruding portion 11a preferably has a ring shape along the outer circumference above the main body lower portion 11. A recessed portion 31a that is to be fit onto the protruding portion 11a of the main body lower portion 11 is provided on the outer circumferential wall 31 of the main body upper portion 12. With this configuration, the outer circumferential wall 31 of the main body upper portion 12 is able to be rotated in the circumferential direction.

Also, a recessed portion 16 that is open upward such that the medicinal liquid pack 20 can be fit therein is provided in the upper surface of the main body lower portion 11. The recessed portion 16 includes a third region R3 that fits together with the first region R1 of the medicinal liquid pack 20 shown in FIGS. 2A and 2B, and a fourth region that fits together with the second region R2 of the medicinal liquid pack 20. Here, the third region R3 is deeper than the fourth region R4. With this configuration, the medicinal liquid pack 20 can be fit into the recessed portion 16. Here, as will be described later in FIG. 6, when the medicinal liquid pack 20 is mounted in the recessed portion 16 of the main body 10, the flange portion 21a of the lid 21 of the medicinal liquid pack 20 is supported by the upper edge 16a of the inner circumferential wall 16c of the main body 10.

Furthermore, a vibration portion 40 is provided on the bottom surface 16b of the fourth region R4 of the recessed portion 16. The vibration portion 40 includes an ultrasonic vibrator 41 provided on the bottom surface 16b of the fourth region R4 of the recessed portion 16, a vibration surface 43 that is provided horizontally at a position corresponding to the bottom surface 16b of the fourth region R4 of the recessed portion 16, and a horn 42 that is located between the ultrasonic vibrator 41 and the vibration surface 43, amplifies the vibration of the ultrasonic vibrator 41, and transmits the vibration to the vibration surface 43. The vibration voltage for the ultrasonic vibrator 41 is supplied from the main body lower portion 11 via a contact electrode provided between the main body upper portion 12 and the main body lower portion 11.

Also, the holder 30 includes an opening 30b through which the medicinal liquid pack 20 is to be removed and inserted, on a portion of the circumferential wall. The circumferential wall of the holder 30 is inserted between the inner circumferential wall 16c and the outer circumferential wall 31. That is, the holder 30 includes a cylindrical circumferential wall that is inserted between the inner circumferential wall 16c and the outer circumferential wall 31, and the holder 30 receives and holds the medicinal liquid pack 20 through the opening 30b in the circumferential wall.

Furthermore, the mesh nebulizer 1 includes an elevator 100 that raises or lowers the holder 30 with respect to the main body 10 accompanying rotation of the outer circumferential wall 31 of the main body 10 about the inner circumferential wall 16c. The elevator 100 preferably includes a first screw 33 provided on the outer circumferential surface of the holder 30, and a second screw 34 provided on the inner surface of the outer circumferential wall 31 of the main body 10 so as to be able to engage with the first screw 33. According to this configuration, when the user rotates the outer circumferential wall 31 of the main body 10 in the circumferential direction (the direction indicated by the arrow A shown in FIG. 1), the holder 30 can be raised. Accordingly, the opening 30b that was hidden inside of the holder 30 can be exposed. Furthermore, when the user rotates the outer circumferential wall of the main body 10 in the circumferential direction (the direction indicated by the arrow A shown in FIG. 1), the holder 30 can be lowered. Accordingly, the opening 30b is located on the inside of the outer circumferential wall 31, and the opening 30b is closed by the outer circumferential wall 31.

Figure 4:
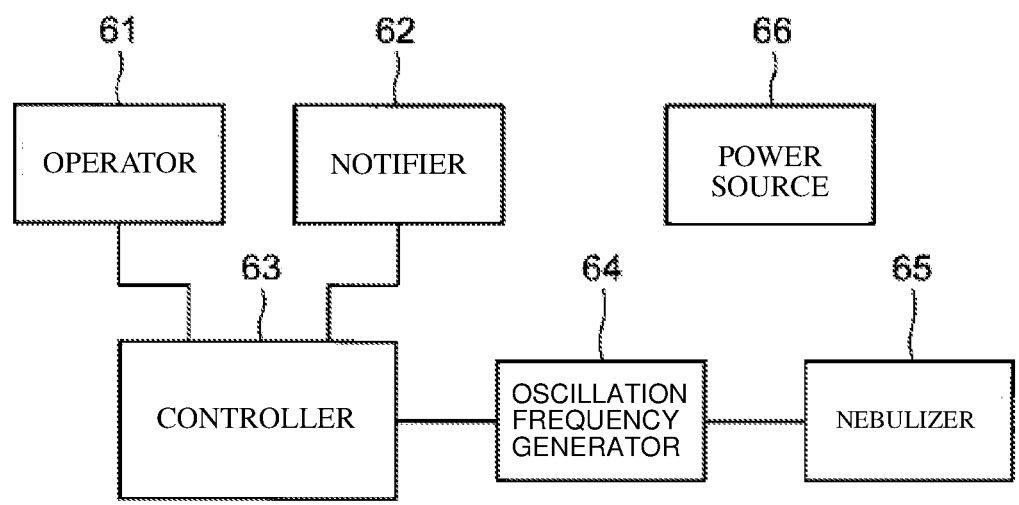
FIG. 4 shows a block configuration of a control system mounted in the main body of the mesh nebulizer shown in FIG. 1.

FIG. 4 shows a block configuration of a control system mounted in the main body 10 of the mesh nebulizer 1. The mesh nebulizer 1 includes an operator 61; a notifier 62; a controller 63; an oscillation frequency generator 64; a nebulizer 65; and a power source 66. In this example, the operator 61 includes the power source switch 50 shown in FIG. 1. The notifier 62 may also include a buzzer (not shown), for example. The oscillation frequency generator 64 applies an AC drive voltage to the nebulizer 65 based on a control signal from the controller 63. The drive voltage is output over a certain output time after the power source switch 50 is pressed, for example. Measurement of the output time can also be performed using a timer (not shown). The nebulizer 65 includes the vibration portion 40 shown in FIG. 1 and the mesh portion 24a of the medicinal liquid pack 20. The AC drive voltage from the oscillation frequency generator 64 is applied to the ultrasonic vibrator 41 of the vibration portion 40 of the nebulizer 65. The vibration of the ultrasonic vibrator 41 is amplified by the horn 42 and is transmitted to the vibration surface 43. When the vibration surface 43 vibrates, the medicinal liquid supplied to the gap between the vibration surface 43 and the mesh portion 24a is nebulized and ejected through the mesh portion 24a. The controller 63 preferably includes a CPU (Central Processing Unit), for example, and transmits signals to the nebulizer 65 via the oscillation frequency generator 64, and thus controls the nebulization amount, continuous operation time, and the like. Also, the controller 63 performs notification of the fact that the power source has been switched on, the fact that the capacity of the battery is insufficient, and the like through illumination or blinking of an LED lamp or the like, for example. The power source 66 includes a battery (e.g., a DC3V chargeable secondary battery) and supplies power to the elements of the control system.

Figure 5:
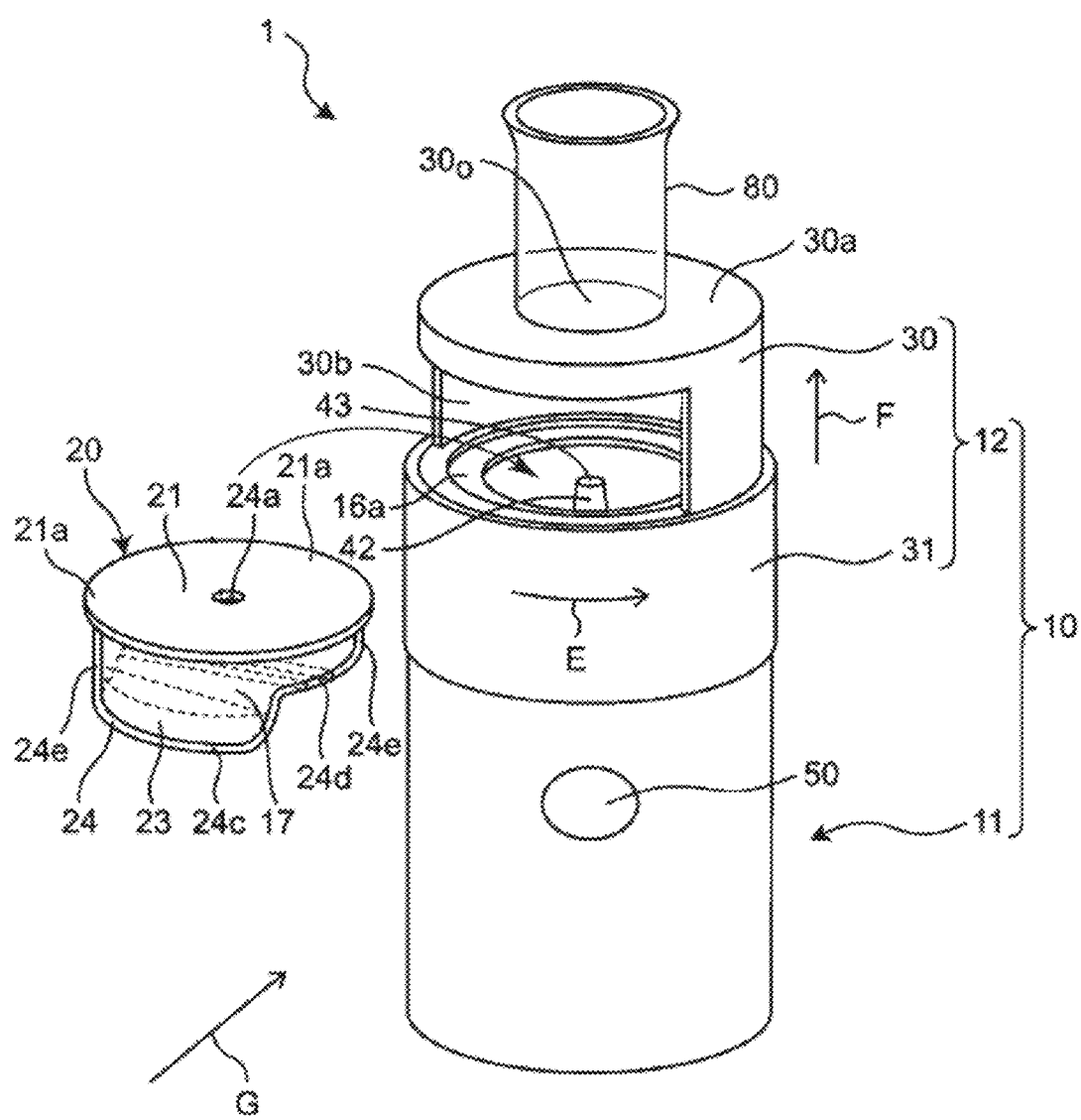
FIG. 5 shows a mesh nebulizer in a state in which an opening of a holder of the mesh nebulizer shown in FIG. 1 is exposed, and a medicinal liquid pack that is to be mounted in a recessed portion of the main body of the mesh nebulizer.

FIG. 5 shows the mesh nebulizer 1 in a state in which the opening 30b of the holder 30 of the mesh nebulizer 1 shown in FIG. 1 is exposed, and the medicinal liquid pack 20 mounted in the recessed portion 16 of the main body 10 of the mesh nebulizer 1. A user who is about to use the mesh nebulizer 1 rotates the outer circumferential wall 31 of the main body 10 in the direction indicated by arrow E, as shown in FIG. 5. Upon doing so, the holder 30, on which the first screw 33, which is engaged with the second screw 34, is provided, rises in the direction indicated by the arrow F, and the opening 30b, which was closed by the outer circumferential wall 31, is exposed. Accordingly, the user causes the medicinal liquid pack 20 to be held by inserting it into the recessed portion 16 of the main body 10 via the opening 30b.

Next, with the medicinal liquid pack 20 mounted in the recessed portion 16, the user rotates the outer circumferential wall 31 of the main body 10 in the direction opposite to that of the arrow E. Upon doing so, the holder 30, on which the first screw 33, which is engaged with the second screw 34, is provided, lowers in the direction opposite to that of arrow F, and the opening 31b is located on the inside of the outer circumferential wall 31. That is, the opening 30b is closed by the outer circumferential wall 31. Accordingly, mounting of the medicinal liquid pack 20 to the mesh nebulizer 1 is complete.

When the medicinal liquid pack 20 is to be mounted in the main body 10, the outer circumferential wall 31 is rotated about the inner circumferential wall 16c, and the holder 30 is lowered with respect to the inner circumferential wall 16c by the elevator 100. Upon doing so, the bottom surface 24c of the recessed portion 17 of the medicinal liquid container 24 of the medicinal liquid pack 20 approaches and comes into contact with the vibration surface 43. Also, the stretchable material of the bottom surface 24c stretches and the vibration surface 43 approaches the mesh portion 24a of the lid 21. Also, when the medicinal liquid pack 20 is to be removed from the main body 10, the outer circumferential wall 31 is rotated about the inner circumferential wall 16c, and the holder 30 is raised with respect to the inner circumferential wall 16c by the elevator 100, and upon doing so, the medicinal liquid pack 20 separates from the vibration surface 43.

Figure 6:
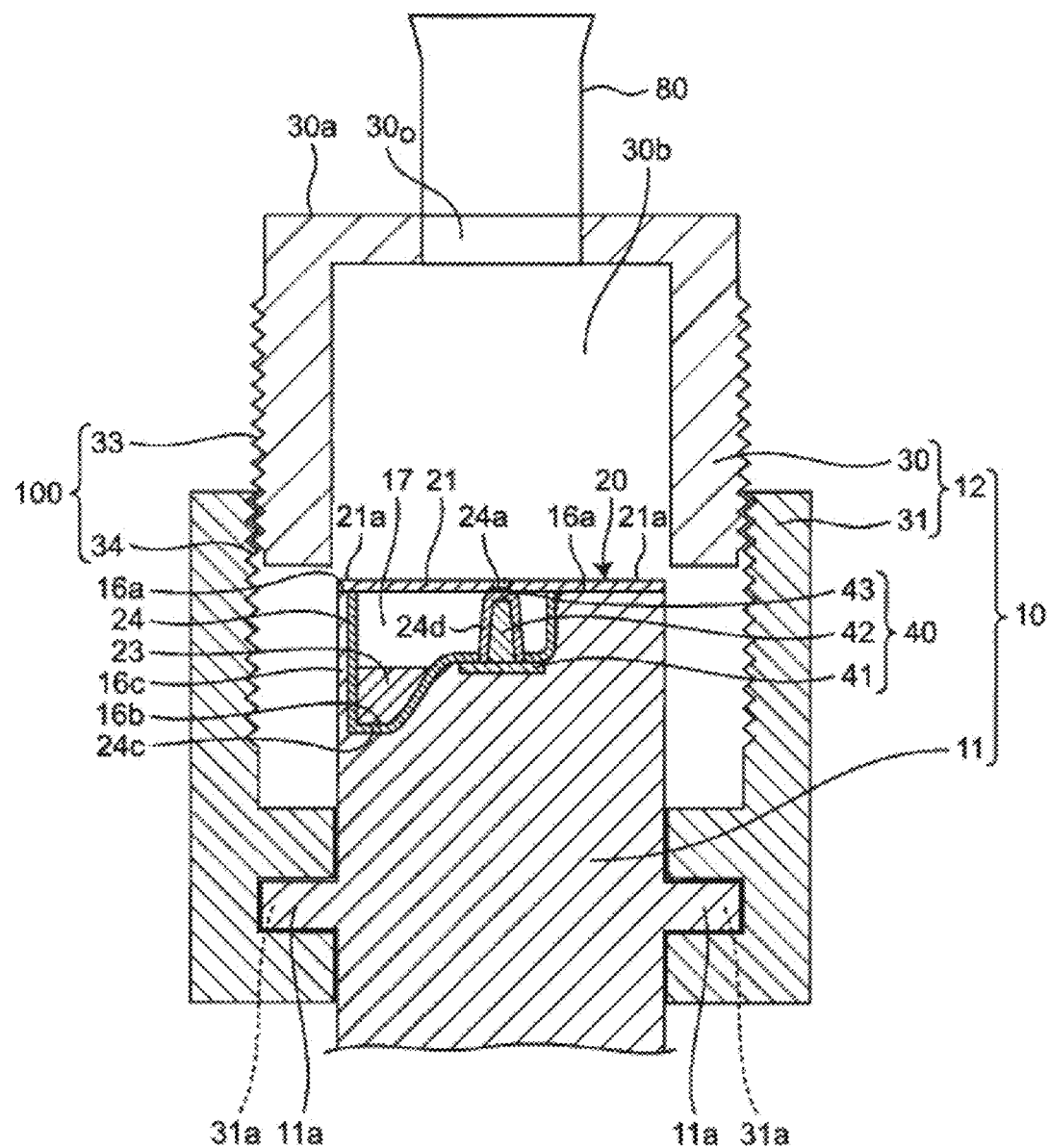
FIG. 6 is a diagram showing a portion of a vertical cross-section of the mesh nebulizer shown in FIG. 5, viewed from the right side.

FIG. 6 is a diagram showing a portion of a vertical cross-section of the mesh nebulizer 1 shown in FIG. 5, viewed from the right side (the direction indicated by the arrow G in FIG. 5). FIG. 6 shows the mesh nebulizer 1 in a state in which the medicinal liquid pack 20 is mounted in the recessed portion 16 of the main body 10 of the mesh nebulizer 1. As shown in FIG. 6, the user mounts the medicinal liquid pack 20 in the recessed portion 16 of the main body 10 via the opening 30b. At this time, the flange portion 21a of the lid 21 of the medicinal liquid pack 20 is supported by the upper edge 16a of the inner circumferential wall 16c of the main body 10.

Also, when the medicinal liquid 20 is mounted in the recessed portion 16 of the main body 10 as shown in FIG. 6, the portion 24d of the bottom surface 24c of the recessed portion 17 of the medicinal liquid container 24 of the medicinal liquid pack 20 that is to oppose the vibration surface 43 stretches, and a state is entered in which the vibration surface 43 has approached the mesh portion 24a of the lid 21.

Figure 7:
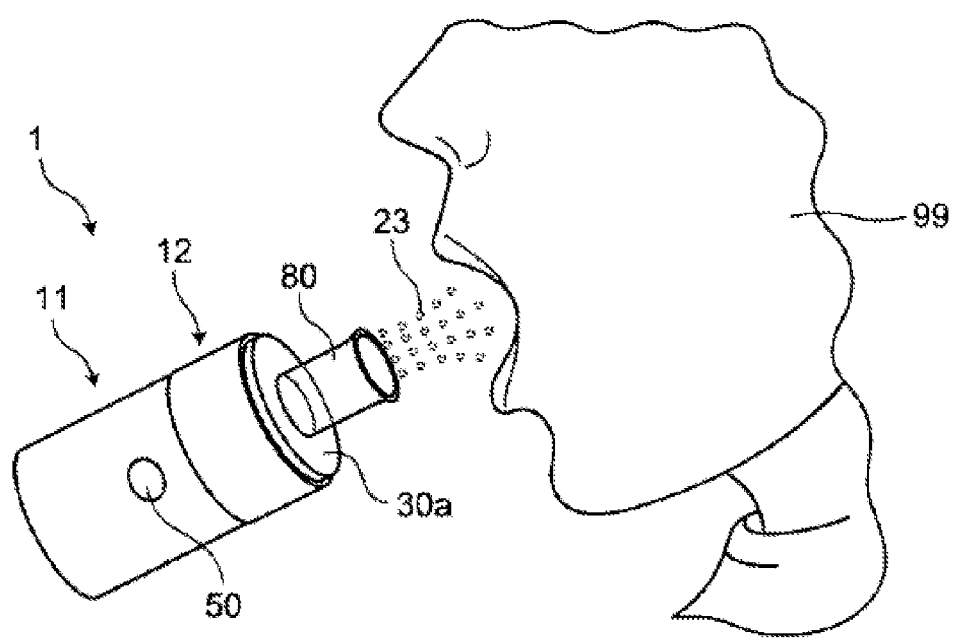
FIG. 7 is a diagram illustrating a user using the mesh nebulizer.

In the case of using the mesh nebulizer 1, the user mounts the medicinal liquid pack 20 through the above-described procedure in advance. Then, as shown in FIG. 7, the user detachably mounts the mouthpiece 80, for example, in the opening 30o provided in the upper surface 30a of the holder 30. Note that instead of the mouthpiece 80, an inhalation mask that covers the face of a user 99 may also be attached.

As shown in FIG. 7, when the user tilts the mesh nebulizer 1 frontward slightly, medicinal liquid 23 in the first region shown in FIG. 2B is supplied onto the vibration surface 43 of the vibration portion 40 along the bottom surface 24c of the recessed portion 17 of the medicinal liquid pack 20. In other words, the medicinal liquid is supplied between the vibration surface 43 and the mesh portion 24a. Then, when the user switches on the power source switch 50, the drive voltage is applied to the ultrasonic vibrator 41 of the vibration portion 40 and the vibration surface 43 is vibrated. Accordingly, the medicinal liquid 23 is nebulized and ejected through the mesh portion 24a.

After use, the medicinal liquid pack 20 is removed from the main body 10 and thrown away.

Thus, since a new medicinal liquid pack 20 is mounted in the mesh nebulizer 1 according to a preferred embodiment of the present invention each time it is used, there is no need to wash the mesh portion 24a. Accordingly, it is hygienic and maintenance is made easier for the user, without reducing the nebulization efficiency. Furthermore, since a new mesh portion 24a is used each time, it is hygienic and the nebulization efficiency does not decrease.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A medicinal liquid pack to be mounted in a mesh nebulizer, the medicinal liquid pack comprising:
   a lid in which a mesh portion is provided; and
   a medicinal liquid container that includes a recessed portion that is open toward the mesh portion and is covered by the lid, the medicinal liquid that is to be supplied onto a vibration surface being contained in the recessed portion; wherein
   at least a portion of a bottom surface of the recessed portion of the medicinal liquid container that is to oppose the vibration surface is made of a stretchable material.

2. The medicinal liquid pack according to claim 1, wherein
   the lid includes a flange portion extending to outside from an upper edge of the medicinal liquid container; and
   when the medicinal liquid pack is mounted on the mesh nebulizer, the flange portion of the lid is supported by an upper edge of an inner circumferential wall surrounding the vibration surface.

3. The medicinal liquid pack according to claim 1, wherein
   the lid has a flat shape;
   the recessed portion includes a deep first region in which the medicinal liquid is stored, and a second region that is shallower than the first region; and
   the bottom surface of the recessed portion of the medicinal liquid container that is to oppose the vibration surface is located in the second region.

4. A mesh nebulizer for nebulizing and ejecting a medicinal liquid through a mesh portion, the mesh nebulizer comprising:
   a main body including a vibration portion including a vibration surface; and
   a medicinal liquid pack to be detachably mounted on the main body; wherein
   the medicinal liquid pack includes:
      a lid in which the mesh portion is provided; and
      a medicinal liquid container that includes a recessed portion that is open toward the mesh portion and is covered by the lid, the medicinal liquid that is to be supplied onto the vibration surface being contained in the recessed portion;
   at least a portion of a bottom surface of the recessed portion of the medicinal liquid container that is to oppose the vibration surface is made of a stretchable material; and
   when the medicinal liquid pack is mounted on the main body, the stretchable material of the bottom surface stretches, allowing the vibration surface to approach the mesh portion of the lid.

5. The mesh nebulizer according to claim 4, wherein the main body further includes:
   an inner circumferential wall surrounding the vibration surface;
   an outer circumferential wall rotatable about the inner circumferential wall concentrically with the inner circumferential wall; and
   a holder that includes a cylindrical circumferential wall that is to be inserted between the inner circumferential wall and the outer circumferential wall and is to receive and hold the medicinal liquid pack through an opening in a portion of the circumferential wall;
   the mesh nebulizer further comprising an elevator to raise or lower the holder with respect to the inner circumferential wall accompanying rotation of the outer circumferential wall of the main body about the inner circumferential wall.

6. The mesh nebulizer according to claim 5, wherein the elevator includes:
   a first screw provided on an outer circumferential surface of the holder; and
   a second screw provided on an inner surface of the outer circumferential wall of the main body so as to be able to engage with the first screw.

* * * * *